United States Patent [19]

Bean et al.

[11] Patent Number: 5,121,062
[45] Date of Patent: Jun. 9, 1992

[54] STREAMING CURRENT DETECTOR PROBE

[75] Inventors: Robert F. Bean, Spring City, Pa.; Steven K. Dentel, Newark, Del.

[73] Assignee: Milton Roy Company, St. Petersburg, Fla.

[21] Appl. No.: 568,589

[22] Filed: Aug. 16, 1990

[51] Int. Cl.$^5$ .............................. G01N 27/60
[52] U.S. Cl. ..................... 324/453; 324/447
[58] Field of Search ........... 324/453, 447, 438, 439, 324/446, 444, 450, 452; 134/1, 143, 184; 204/280, 193

[56] References Cited

U.S. PATENT DOCUMENTS

| | | | |
|---|---|---|---|
| 3,368,145 | 2/1968 | Gerdes | 324/453 |
| 3,369,984 | 2/1990 | Gerdes | 204/400 |
| 3,399,133 | 8/1968 | Gerdes et al. | 210/709 |
| 3,614,602 | 10/1971 | Ciotti | 324/453 |
| 4,446,435 | 5/1984 | Canzoneri | 324/453 |
| 4,769,608 | 9/1988 | Bryant | 324/453 |
| 4,825,169 | 4/1989 | Carver | 324/453 |
| 4,961,147 | 10/1990 | Moore | 324/453 X |

Primary Examiner—Kenneth A. Wieder
Attorney, Agent, or Firm—Woodcock Washburn Kurtz Mackiewicz & Norris

[57] ABSTRACT

A streaming current detector has a reciprocating piston with a sensing region having a uniform clearance from the casing which is sufficiently large to avoid significant shearing of the particles in the fluid of the sample stream. A separate guiding region of the piston has a sufficiently tight fit in the casing for smooth reciprocation. A relief region of the piston has the largest clearance from the casing to provide a sufficiently large area to control a constant low velocity of the sample fluid.

8 Claims, 2 Drawing Sheets

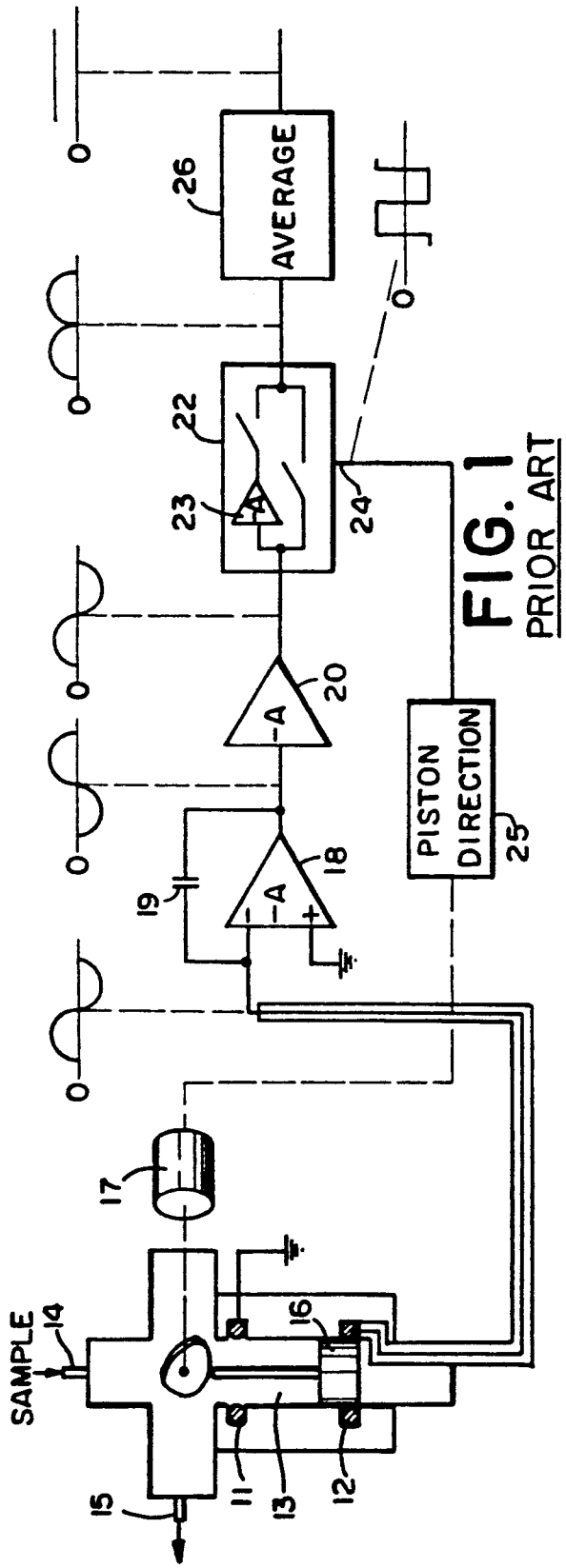
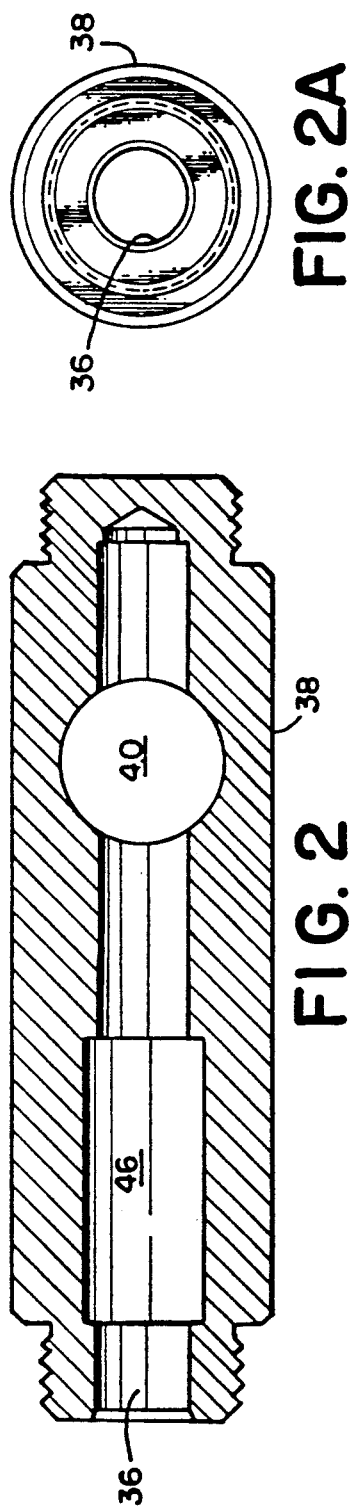

STREAMING CURRENT DETECTOR PROBE

BACKGROUND OF THE INVENTION

This invention relates to streaming current detectors, and more particularly, to an improved probe which substantially avoids shearing of the fluid particles in such a detector.

General Background

Streaming current detectors measure the charge on particles in a fluid sample stream.

U.S. Pat. Nos. 3,368,144, 3,368,145 and 3,369,984-Gerdes, et al and U.S. Pat. No. 3,911,133-Gerdes, et al show streaming current detectors. U.S. Pat. No. 4,446,435-Canzoneri and U.S. Pat. No. 4,825,169-Carver show improvement on the streaming current detector.

In the instruments shown and described in these patents, a reciprocating measuring piston moves a sample fluid past measuring electrodes. Lands and grooves are formed on the surface of the piston. A very small annular clearance is maintained between the lands and the piston bore in order to obtain guidance of the piston. This is described in U.S. Pat. No. 4,446,435, Col. 5, lines 21-28 and in FIG. 3 which shows the lands 43. The small annular clearance (typically 0.005 inch) between the lands and the piston bore have caused shearing of the particles in the sample fluid. Typically, particles in a waste water sample stream have particles of approximately 0.005 inch in diameter. When these particles are sheared, the surface charge will be altered due to newly exposed surface areas, and an erroneous measurement of surface particle charge is produced.

Also, the construction of the piston is easier to machine if the lands could be eliminated and/or if the clearance of the piston could be significantly increased.

SUMMARY OF THE INVENTION

In accordance with the present invention, a piston in a streaming current detector has a guiding region which is separate from the sensing region in which the electrodes are disposed.

The improved construction results in noticeably less shearing and cleavage of flocculated/coagulated particles in the sample of suspension being tested. This means that the sample in the instrument is more closely representative of the mass of fluid to be treated with flocculating chemical(s), and the reading which the streaming current instrument displays is therefore more accurate and consistent. These more accurate readings generally result in more accurate treatment of sample fluid.

Long term accuracy and reliability of the instrument are improved because the piston and bore are not sensitive to the wear which results from particle abrasion after a period of extended use when there are lands and grooves. This is because the wear is localized near the lands and a pair of parts become "worn in" in a particular angular relationship which, if not maintained, introduces instrument error. The improved construction is superior in this regard in two ways, namely that: 1) because of the greater clearance, it is subject to a lower rate of wear, and that: 2) any wear which does occur has far less effect on instrument accuracy.

The foregoing and other objects, features and advantages of the invention will be better understood from the following more detailed description and appended claims.

DESCRIPTION OF THE DRAWINGS

FIG. 1 shows a prior art streaming current detector;
FIG. 2 is a cross-section through the piston casing;
FIG. 2A is an end view of the casing.

DESCRIPTION OF THE PREFERRED EMBODIMENT

Figure 3:
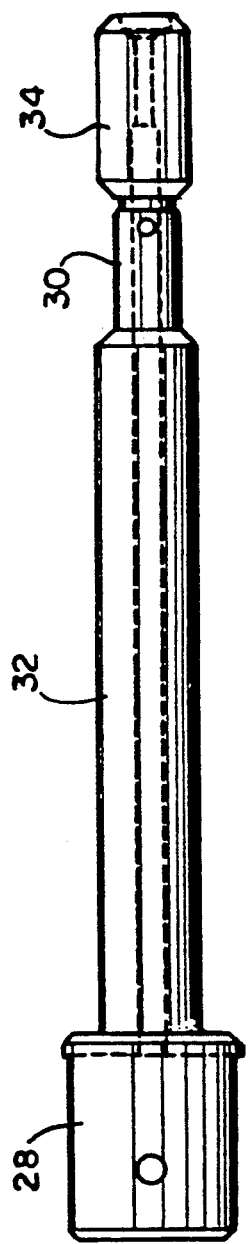
FIG. 3 shows the piston.

FIG. 1 shows a typical streaming current detector. A pair of electrodes 11 and 12 are disposed in a bore 13. Sample fluid flows through inlet 14 and outlet 15. A piston 16 reciprocates in the bore between electrodes 11 and 12, thereby pushing sample fluid past the electrodes first in one direction and then in the other direction.

Lands (not shown) on the piston surface guide the piston. A motor 17 has a shaft connected to an eccentric or the like which reciprocates the piston 16 in the bore.

Electrodes 11 and 12 are connected through coaxial cable to the amplifying circuitry which includes operational amplifier 18. The output of operational amplifier 18 is further amplified in amplifier 20, the output of which is applied to the input of rectifier 22. Rectifier 22 is an electronic synchronous detector which includes operational amplifier 23. The output signal from amplifier 20 is directed to both the inverting and non-inverting inputs of rectifier 22. Electronic switches consisting of field effect transistors are appropriately connected by a control port 24 through which the selection of inverting or non-inverting amplification can be made by remote electrical signals.

The control port 24 of rectifier 22 is connected to the output of piston direction generator 25 which may typically be the light detector and light source shown in the Carver U.S. Pat. No. 4,825,169. Piston direction generator 25 generates a piston direction signal in synchronism with the reciprocation of piston 16.

The output of rectifier 22 is applied to an averaging circuit 26 which produces an output proportional to the charge of the sample fluid.

Figure 4:
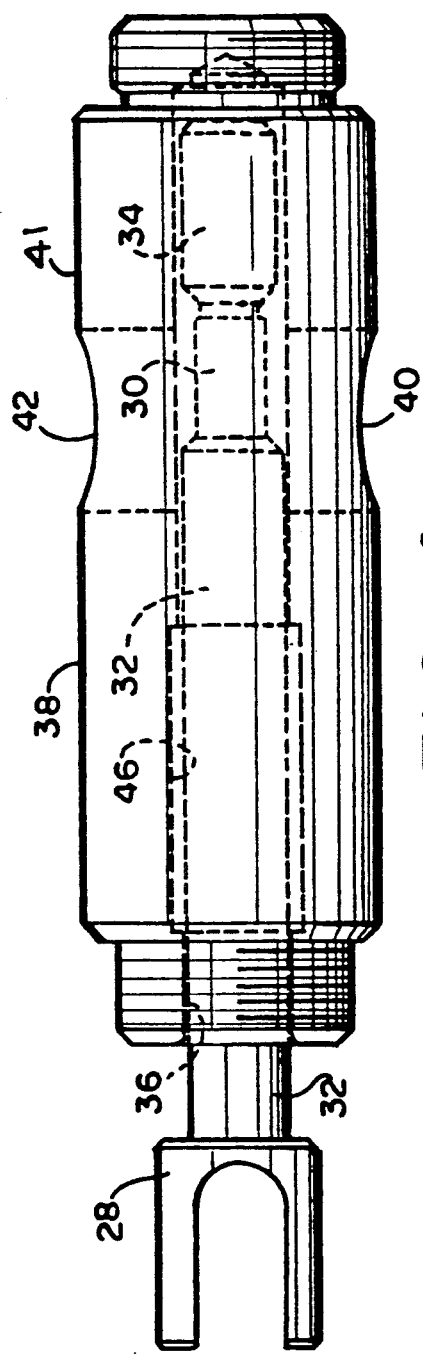
FIG. 4 is a cross-section through the casing with the piston therein.

The present invention is shown in FIGS. 2-4. Piston 28 has a sensing region 34, relief region 30 and guiding region 32. Piston 28 reciprocates in the bore 36 of casing 38.

In accordance with the invention, the sensing region 34 has a uniform clearance from the casing in the region in which it travels. This clearance is sufficiently large to avoid substantial amounts of shearing of particles in the fluid in this region. Typically, a bore of approximately ⅜" diameter, has a uniform piston clearance of approximately 1/64" in the sensing region.

It has been found that improved streaming current detection with such a device is attributable to the significant reduction of particle shearing in the sample stream. A clearance of up to 0.25" inch may be used in accordance with the invention. The clearance in the sensing region 34 is greater than the casing clearance throughout the travel of guiding region 32. The clearance between the guiding region and the bore is sufficiently tight to provide smooth reciprocation, typically, approximately 0.0025 inches clearance is provided.

An inlet port 40 and an outlet port 42 provide flow of a sample stream of the fluid through the casing where the sensing region of the piston reciprocates. The relief region 30 of the piston provides more area for a constant low velocity of the sample fluid in the sensing region 41 in the casing as the piston reciprocates. The low velocity of the fluid produces less current to be detected by the electrodes, but a higher velocity causes more shearing of the particles in the fluid. Thus, the relief region 30 is designed to maintain a low velocity to cause sufficiently detectable current with minimal shearing of particles in the fluid for accurate readings.

The electrodes may be disposed in the casing in the sensing region 41 of the casing. The electrodes 11 and 12 are disposed where the sensing region 34 of the piston reciprocates. In accordance with the present invention, the electrodes 11a and 12a are placed on the surface of sensing region 34 of the piston. Location of the electrodes on the piston has an advantage over the prior art in that the moving electrodes help substantially reduce covering of electrodes by flocculated particles.

A yoke on the end of the piston is attached to an eccentric or other means for reciprocating the piston.

The bore 36 in casing 38 is of greater diameter in the region marked 46. The region 46 does not have any functional significance, but it reduces the manufacturing cost.

While a particular embodiment of the invention has been shown and described, various other modifications are within the true spirit and scope of the invention. The appended claims are, therefore, intended to cover all such modifications.

What is claimed is:

1. A streaming current detector for determining the charge condition in a fluid containing particles comprising:
    a reciprocating piston;
    a casing in which said piston reciprocates;
    said piston having a sensing region and a guiding region which is separated form said sensing region, said fluid being in said casing where said sensing region reciprocates;
    said sensing region having a uniform clearance from said casing, said clearance being sufficiently large to avoid significant shearing of said particles in said fluid the clearance of said sensing region being sufficiently greater than the clearance between said piston and said casing in said guiding region to prevent significant shearing of said particles where said sensing region reciprocates; and
    electrodes disposed where said sensing region of said piston reciprocates for detecting a streaming current signal.

2. The streaming current detector recited in claim 1 wherein said piston has a uniform diameter in said guiding region and a smaller uniform diameter in said sensing region.

3. The streaming current detector recited in claim 1 wherein said casing has a cylindrical bore in which said piston reciprocates, said bore having a uniform diameter throughout the travel of said guiding region and a uniform diameter throughout the travel of said sensing region of said piston.

4. The streaming current detector recited in claim 1 wherein said piston has a uniform diameter relief region with a smaller uniform diameter in said relief region than in said sensing region.

5. The streaming current detector recited in claim 1 wherein the clearance between said casing and said piston in the guiding region thereof is sufficiently tight to provide smooth reciprocation of said piston.

6. The streaming current detector recited in claim 4 further comprising:
    an inlet port in said casing where said relief region of said piston reciprocates;
    an outlet port in said casing where said relief region of said piston reciprocates;
    said fluid flowing in a sample stream between said inlet port and said outlet port.

7. The streaming current detector recited in claim 1 wherein said electrodes are mounted on the surface of said piston in said sensing region for measuring said streaming current signal.

8. The streaming current detector recited in claim 4 wherein said relief region of said piston controls a constant low velocity of said fluid in said sensing region, said low velocity causing a measurable streaming current signal but avoiding significant shearing of said particles in said fluid at a higher velocity.

* * * * *